United States Patent [19]
Reiter et al.

[11] Patent Number: 6,048,489
[45] Date of Patent: Apr. 11, 2000

[54] ABSORBENT PRODUCTS, AND APPARATUS AND METHOD FOR PRODUCING THE SAME

[75] Inventors: Godfrey Reiter, Cincinnati; John Billings Burchnall, West Chester, both of Ohio

[73] Assignee: The Procter & Gamble Company, Cincinnati, Ohio

[21] Appl. No.: 09/240,970

[22] Filed: Jan. 29, 1999

Related U.S. Application Data

[62] Division of application No. 08/752,163, Nov. 18, 1996, Pat. No. 5,866,173.

[51] Int. Cl.⁷ .................................................. B27N 3/02
[52] U.S. Cl. ......................... 264/510; 264/517; 264/113
[58] Field of Search .................................... 264/510, 517, 264/113

[56] References Cited

U.S. PATENT DOCUMENTS

| | | |
|---|---|---|
| 3,344,789 | 10/1967 | Arnold et al. . |
| 3,667,258 | 6/1972 | Newton . |
| 3,717,905 | 2/1973 | Furbeck . |
| 3,888,257 | 6/1975 | Cook et al. . |
| 4,054,628 | 10/1977 | Marshall . |
| 4,070,235 | 1/1978 | Marshall . |
| 4,073,852 | 2/1978 | Mesek . |
| 4,600,458 | 7/1986 | Kramer et al. . |
| 4,610,678 | 9/1986 | Weisman et al. . |
| 4,666,647 | 5/1987 | Enloe et al. . |
| 4,765,780 | 8/1988 | Angstadt ................................. 264/517 |
| 4,865,596 | 9/1989 | Weisman et al. . |
| 4,888,231 | 12/1989 | Angstadt . |
| 4,927,346 | 5/1990 | Kaiser et al. ........................... 425/81.1 |
| 4,927,582 | 5/1990 | Bryson .................................... 264/113 |
| 5,076,774 | 12/1991 | Farrington et al. .................... 425/82.1 |
| 5,102,585 | 4/1992 | Pieper et al. . |
| 5,248,524 | 9/1993 | Soderlund .............................. 427/400 |
| 5,334,177 | 8/1994 | Cohen .................................... 604/378 |
| 5,429,788 | 7/1995 | Ribble et al. .......................... 264/510 |
| 5,433,715 | 7/1995 | Tanzer et al. .......................... 604/368 |
| 5,447,677 | 9/1995 | Griffoul et al. ........................ 264/510 |

FOREIGN PATENT DOCUMENTS

| | | |
|---|---|---|
| WO 8001455 | 7/1980 | WIPO . |
| WO 9109580 | 7/1991 | WIPO . |
| WO 9118137 | 11/1991 | WIPO . |
| WO 9613335 | 5/1996 | WIPO . |

*Primary Examiner*—Mary Lynn Theisen
*Attorney, Agent, or Firm*—David M. Weirich; Steven W. Miller; Jacobus C. Rasser

[57] ABSTRACT

An absorbent core for use in an absorbent article for absorbing discharged bodily fluid comprises a first absorbent material dispersed throughout the core, and a second absorbent material provided in a discrete strip, and substantially surrounded by the first absorbent material. An apparatus and method for producing such cores comprises a mold support advanceable in a predetermined direction and having at least one mold therein, and a tubular conduit for the second material alignably positioned such that a portion of the conduit will pass through at least a portion of the mold as the mold support is advanced. The mold support may comprise a forming drum or a forming belt. The tubular conduit has a distal end through which the second absorbent material may be expelled. Particles of the first absorbent material are preferably deposited by air-entrainment into the molds, and these particles surround the tubular conduit in order to form a cavity into which the second absorbent material is deposited from the distal end of the conduit.

19 Claims, 5 Drawing Sheets

ABSORBENT PRODUCTS, AND APPARATUS AND METHOD FOR PRODUCING THE SAME

This application is being filed under 37 CFR 1.60 as a divisional application of U.S. patent application Ser. No. 08/752163 which was filed on Nov. 18, 1996, now U.S. Pat. No. 5,866,173.

BACKGROUND OF THE INVENTION

1. Field of the Invention

This invention relates to absorbent articles, as well as to an apparatus and method for producing absorbent articles. More particularly, the present invention provides absorbent cores made from two or more absorbent materials, wherein at least one of these absorbent materials is provided in one or more strips.

2. Description of Related Art

Absorbent articles for the absorption and retention of discharged bodily fluids (urine, blood, vaginal discharge, etc.) are well known in the prior art, and generally include an absorbent core having one or more absorbent materials therein. In the case of diapers, incontinence pads, sanitary napkins, pantiliners and the like, the absorbent core is generally disposed between a topsheet and a backsheet. The topsheet is fluid pervious, and allows discharged fluids to pass therethrough for absorption by the core. The backsheet is generally fluid impervious, and prevents absorbed fluids from escaping the absorbent article.

Various types of absorbent materials may be incorporated into the core of the article, particularly cellulosic fibers such as wood pulp. Recently, superabsorbent polymers also known as absorbent gelling materials (AGM's) have been developed which can be incorporated into absorbent cores for improved performance. AGM's are polymeric materials which are capable of absorbing large quantities of fluids to form hydrogels and which are further capable of retaining the absorbed fluids under moderate pressures. Typically, the AGM is incorporated along with one or more conventional fibrous materials, often in multi-layer configurations. For example, the absorbent core of an absorbent article may comprise one layer consisting solely of cellulosic fibers, and a second layer consisting of a uniform combination of cellulosic fibers and AGM particles.

Manufacturing multi-component absorbent cores can be difficult and expensive, and often requires two or more separate core-making apparatus. While various apparatus for overcoming this problem have been suggested, such as that disclosed in U.S. Pat. No. 5,447,677, it is often difficult to control the amount and location of AGM deposition in such apparatus. Since AGM's are significantly more expensive than more traditional fibrous materials, it is advantageous to insure that the amount and location of AGM is precisely controlled. Such control is difficult, however, with conventional air-laying apparatus.

Precise control of the amount and location of AGM within the core is desirable not only due to costs, but also for improved performance. While AGM's rapidly absorb many times their weight in fluids, they are subject to gel-blocking. Gel-blocking occurs when the surface of an AGM particle, film, or fiber rapidly swells with absorbed fluid and prevents fluid transmission to the interior of the particle, film or fiber. When this occurs, wetting of the interior takes place via a very slow diffusion process, and the absorbent article may fail well before the AGM has reached its fluid capacity.

Thus, there is a need for absorbent articles having a first absorbent material such as cellulosic fibers, and a second absorbent material, such as an AGM, wherein the second material is selectively provided in at least one strip within the first material, as well as an apparatus and method for producing such absorbent articles.

SUMMARY OF THE INVENTION

It is an object of the present invention to provide absorbent cores for use in absorbent articles such as diapers, incontinence pads, sanitary napkins, pantiliners and the like, wherein an absorbent material such as AGM is positioned only where needed for optimal performance.

It is another object of the present invention to provide absorbent cores wherein an absorbent material such as AGM is provided in one or more strips extending substantially lengthwise through the core, wherein the AGM is surrounded by another absorbent material such as cellulosic fibers.

It is yet another object of the present invention to provide an apparatus and method for producing such cores.

The foregoing objects can be accomplished, in accordance with one aspect of the present invention by providing an absorbent core for use in an absorbent article for absorbing discharged bodily fluid, wherein the core comprises:

(a) a first absorbent material dispersed substantially within the core; and (b) a second absorbent material provided in one or more discrete strips which are substantially surrounded by the first absorbent material. The strips of second absorbent material preferably extend substantially lengthwise within the core. One or more of the strips may also be discontinuous, thereby comprising a plurality of co-linear segments. The first absorbent material preferably comprises cellulosic fibers, and the second absorbent material preferably comprises an absorbent gelling material ("AGM") . Other types of absorbent materials, however, may be employed for either of the absorbent materials.

The absorbent cores of the present invention can be produced by an apparatus comprising:

(a) a mold support advanceable in a predetermined direction and having at least one mold therein; and (b) a tubular conduit for the second material alignably positioned such that a portion of the conduit will pass through at least a portion of the mold as the mold support is advanced.

The mold support may comprise a forming belt, preferably continuous and advanceable in a closed-loop fashion (i.e., a conveyor belt having one or more molds in its surface). Preferably, however, the mold support comprises a forming drum. A single mold may extend about at least a portion of the circumference of the forming drum, or even the entire forming drum. In the latter case, the mold may be used to produce a plurality of absorbent cores by cutting the strip of absorbent core material produced by such a drum. Preferably, however, a plurality of molds are provided about the circumference of the drum. Each of the molds preferably has endwalls and a bottom surface, and a passageway extends between the endwalls of each pair of adjacent molds. These passageways are preferably circumferentially aligned with one another. The tubular conduit preferably has an arcuate segment, wherein the arcuate segment extends about a portion of the drum and is alignably positioned such that the arcuate segment will pass through at least a portion of the passageways and at least a portion of the molds as said forming drum is rotated. A source for the second material (such as a dispenser or injector) in fluid communication with the conduit is also preferably provided, along with a deposition chute adjacent the forming drum for presenting the first material to the molds.

Preferably, a plurality of tubular conduits are provided, each having an arcuate segment which extends about a portion of the drum and is alignably positioned such that said arcuate segment will pass through at least a portion of the passageways and at least a portion of the molds as the forming drum is rotated. Additionally, a plurality of passageways extending between the endwalls of each pair of adjacent molds are provided, wherein each passageway extending from one endwall of a mold is aligned with another passageway extending from the opposite endwall of the mold. In this fashion, each arcuate segment may "ride" within its own passageway between molds, as the drum is rotated. Thus, the number and spacing of passageways preferably corresponds to the number and spacing of arcuate segments, however it is also possible that more than one arcuate segment may "ride" within a single passageway. It is also preferred that the curvature of the arcuate segments of the tubular conduits corresponds to the curvature of the forming drum, such that the forming drum may be freely rotated about its axis with the arcuate segments positioned at a substantially constant depth within the molds as the drum is rotated.

The interior of the forming drum is maintained under a pressure differential, such that the interior pressure is less than that within the molds. This may be accomplished by means well-known in the art, and the interior of the drum is most preferably maintained under vacuum. The bottom surface of the molds is foraminous and thus provides fluid communication between the molds and the interior of the drum, which in turn provides a suction force for drawing absorbent material into the molds. The deposition chute has a hood positioned adjacent the forming drum, and this hood is configured so as to direct fluid-entrained (preferably air-entrained) particles of the first absorbent material conducted through the chute into the molds. The arcuate segments are preferably at least as long as the length of a single mold. The portion of the forming drum located beneath the hood defines a absorbent laydown region having an entrance and an exit, wherein normal rotation of the drum causes the molds to move through the absorbent laydown region from the entrance towards the exit. The tubular conduits are configured such that the arcuate segments extend about the surface of the drum from a point prior to the entrance of the absorbent laydown region, and preferably extend a small distance beyond the absorbent laydown region. The arcuate segments may, however, terminate within the laydown region, preferably at a point beyond which the first material has fully covered the tubular conduit. This is particularly useful when the second material is to be pulsed through the tubular conduit in order to produce discontinuous strips of the second absorbent material comprising a plurality of co-linear segments, since the first absorbent material may then fill the gaps between the segments of second absorbent material.

The tubular conduits may be made of any of a number of materials, and have a variety of cross-sectional shapes. The shape of the distal ends of the tubular conduits, as well as the cross-sectional shape and dimensions of the portion of the conduit which passes through the mold(s), will largely define the cross-sectional shape of the strips of second absorbent material. The passageways for the arcuate segments are preferably shallower than the molds, thereby ensuring that the arcuate segments are elevated above the bottom surface of the molds. In fact, it is also possible that the arcuate segments are elevated above the bottom surface of the molds at different heights. Thus, one of the arcuate segments may be positioned at a first height above the bottom surface of the molds as the drum is rotated, and another of the arcuate segments may be positioned at a second height above the bottom surface of the molds as the drum is rotated, wherein the first height is different from the second height.

The present invention also provides a method of producing the absorbent cores using the above-described apparatus. Particles of the first absorbent material (such as cellulosic fibers) are fluid-entrained and blown through the chute into the absorbent laydown region. Here the particles are deposited into the mold(s) advancing or rotating through the region where they are preferably held in place by the pressure differential acting through the foraminous bottom surface of the molds. Since a portion of the tubular conduit (e.g., an arcuate segment) is present in the molds in the absorbent laydown region, the particles will be deposited substantially about the circumference of the tubular conduit, thereby forming a cavity which substantially surrounds the tubular conduit. As the molds advance or rotate out of the absorbent laydown region, the second absorbent material will be urged from the distal end of the tubular conduit into the cavities. Preferably, the distal end of the tubular conduit is positioned after the absorbent laydown region in order to ensure complete formation of the cavities and to minimize unneeded deposition of the first absorbent material. Alternatively, the distal end may end may be positioned within the laydown region, particularly when the second absorbent material is pulsed through the tubular conduit in order to provide a discontinuous strip of second absorbent material.

BRIEF DESCRIPTION OF THE DRAWINGS

While the specification concludes with claims particularly pointing out and distinctly claiming the present invention, it is believed that the same will be better understood from the following description read in conjunction with the accompanying drawings in which:

DESCRIPTION OF THE PREFERRED EMBODIMENTS

Figure 3:
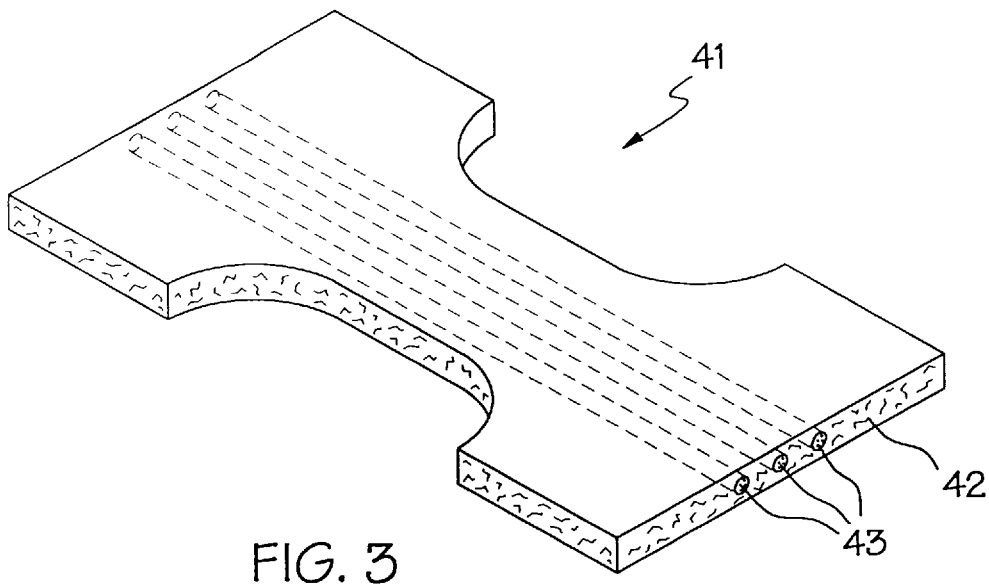
FIG. 3 is a perspective view of an absorbent core for a diaper produced using the apparatus and method of the present invention.

FIG. 3 depicts an exemplary absorbent core 41 for a disposable diaper, wherein core 41 has been produced by the apparatus and methods of the present invention. Absorbent core 41 comprises a first material 42 distributed within the core (preferably at least substantially throughout the entire core), and a second absorbent material 43 which extends generally lengthwise across core 41 in a plurality of strips. The strips preferably extend in the "machine direction" (M.D.), or parallel to the normal direction of travel of absorbent core 41 during manufacturing. Strips of second absorbent material 43 are shown as having a circular cross-section, however, as will be more fully understood below, various other cross-sectional shapes may be employed. Additionally, diaper core 41 is shown as having three strips of second material 43 spaced evenly across the central portion of core 41 at approximately the same elevation within the core, however, various alternative configurations can be employed. For example, the number of strips may be readily varied as needed, and the lateral location and elevation of the strips can also be modified. First absorbent material 42 may be of any conventional material used for this purpose, such as cellulosic fibers. Likewise, second absorbent material 43 may also be any material commonly used in such products, and is preferably an absorbent gelling material (AGM) either alone or in combination with cellulosic fibers.

Figure 4:
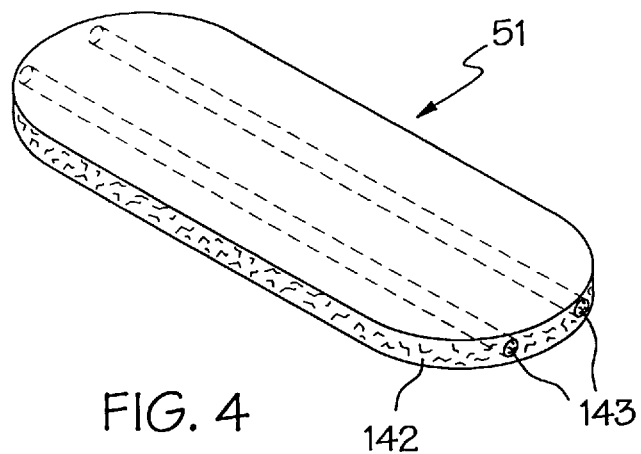
FIG. 4 is a perspective view of an absorbent core for a sanitary napkin produced using the method and apparatus of the present invention.

FIG. 4 discloses an absorbent core 51 for a sanitary napkin produced by the apparatus and methods of the present invention. Like diaper core 41, sanitary napkin core 51 comprises a first absorbent material 142 disbursed throughout the core and a plurality of strips of second material 143 extending lengthwise within core 51. Once again various configurations for these strips for second material 143 may be employed, and thus the number, size, location, elevation and cross-sectional shape may be varied considerably from that shown.

Figure 5:
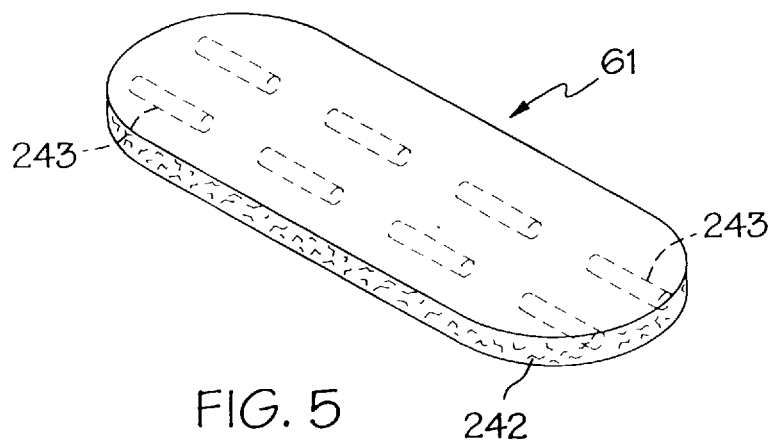
FIG. 5 is a perspective view of yet another absorbent core for a sanitary napkin produced using the method and apparatus of the present invention.

FIG. 5 shows yet another absorbent core 61 for a sanitary napkin produced by the apparatus and methods of the present invention. In this embodiment, first absorbent material 242 is distributed throughout the core, and a plurality of discontinuous (i.e., segmented) strips of second material 243 extend lengthwise within core 251. In this manner, each strip of second material 243 comprises a series of co-linear segments (i.e., a discontinuous strip). The different embodiments for the strips of second absorbent material may also be combined with one another, such that a single core may have one or more continuous strips, along with one or more discontinuous strips comprising a plurality of co-linear segments. Thus, the performance properties of the core can be precisely tailored to the particular application.

The absorbent cores of the present invention are particularly advantageous because, unlike the cores of the prior art, the location of second absorbent material 43 can be precisely controlled. The apparatus and methods of the prior art generally require that a second absorbent material such as AGM be distributed throughout the entire core, in a large region of the core, or in a separate layer. The absorbent cores of the present invention have discrete strips of the second absorbent material which are at least partially surrounded by the first absorbent material, thereby providing greater control over the absorbent properties of the core. For example, when AGM is employed as the second absorbent material and cellulosic fibers as the first absorbent material, fluids are first acquired by the cellulosic fibers. The fluids are then wicked throughout the cellulosic fibers to thereby present fluids to the AGM about the entire circumference of the AGM strip. In this manner, the AGM strips can absorb fluids radially inward from about their entire circumference of the strip, thereby lessening the likelihood of gel block and improving the efficiency of the core. Less AGM can also be employed because of the improved efficiency, thereby providing a less expensive core.

Targeting the AGM in one or more strips extending across the core also allows the AGM to be placed only in the areas having the highest fluid load, thereby further improving the efficiency of AGM utilization. The depth of the AGM can also be precisely controlled, which in turn leads to a dryer product since most of the discharged fluids will be stored in the AGM strips. The AGM strips also create fluid directing channels which prevent side soiling and leakage, particularly when provided in "MD" orientation. Suitable AGM's include silica gels and organic compounds such as crosslinked polymers. Particularly preferred AGM's include hydrolyzed acrylonitrile grafted starch, acrylic acid grafted starch, polyacrylates, isobutylene maleic anhydride copolymers, and mixtures thereof. AGM's disclosed in U.S. Pat. No. 5,360,420, which is incorporated herein by reference, may also be employed. One presently preferred AGM is Nalco 1180, a polyacrylate manufactured by the Nalco Chemical Co., of Naperville, Ill.

Figure 1:
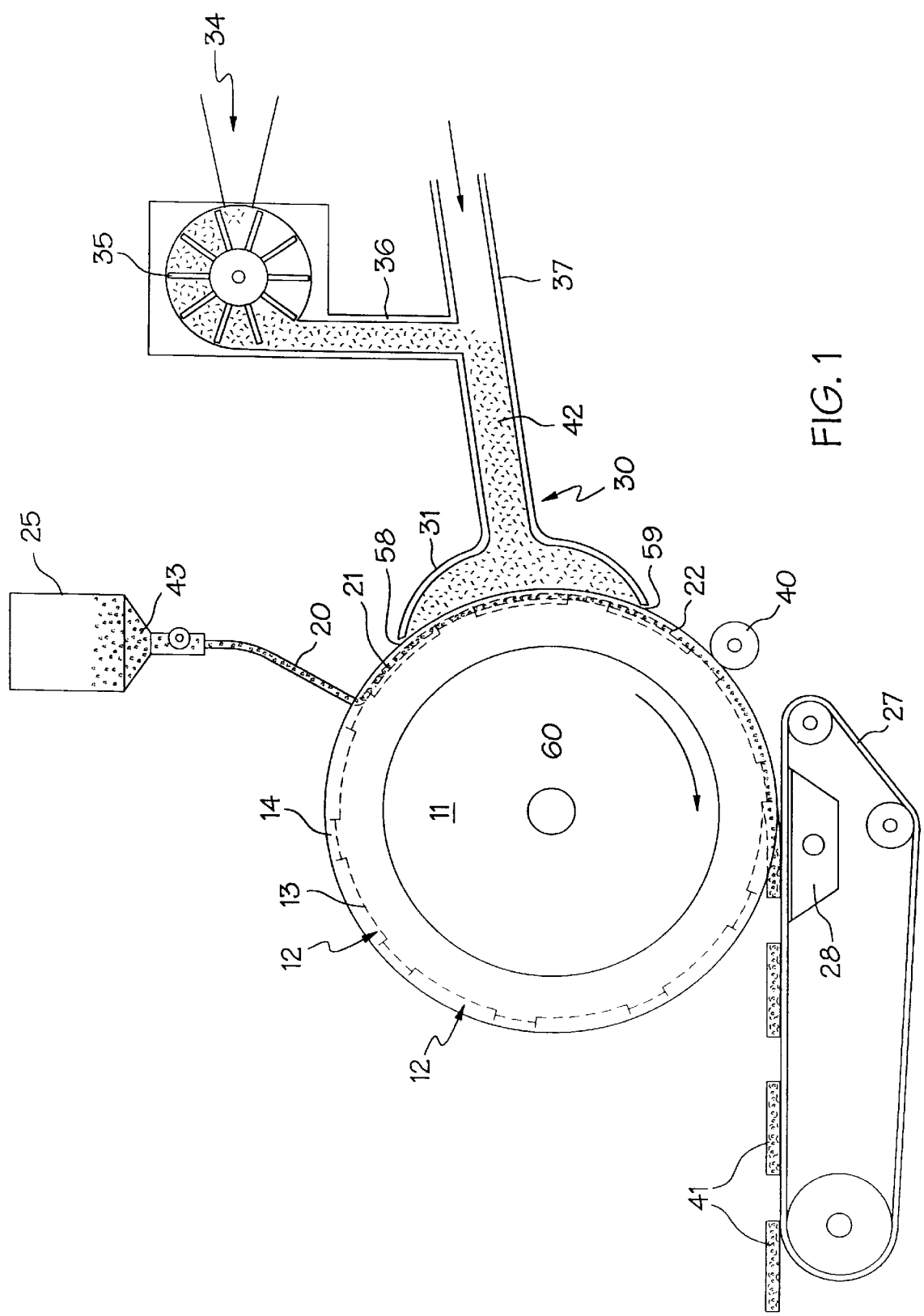
FIG. 1 is a schematic illustration of the apparatus of the present invention.
Figure 2:
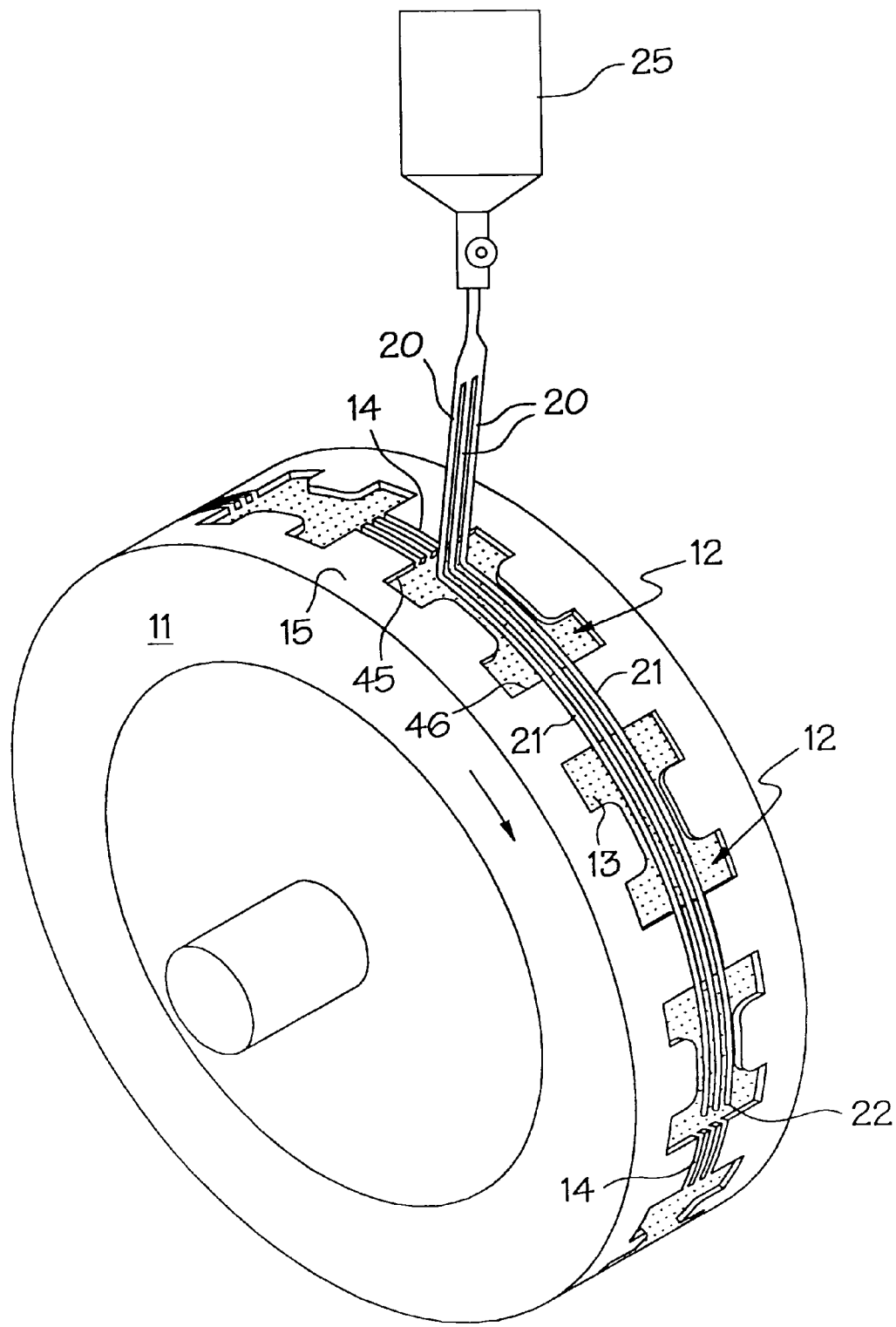
FIG. 2 is a perspective view of the forming drum, tubular conduit and dispenser of the present invention.

The absorbent cores of FIGS. 3 and 4 may be produced by the apparatus shown in FIGS. 1–2 and 6–7, wherein an advanceable mold support having at least one mold therein is provided. In the embodiment of FIGS. 1–2, the mold support comprises cylindrical forming drum 11, the interior of which is preferably maintained under a pressure differential (and most preferably under vacuum) by conventional means. Preferably, a plurality of molds 12 are aligned about the circumference of forming drum 11, as is well-known in the art. Each mold 12 has first and second endwalls 45 and 46, respectively, and a bottom surface 13. Molds 12 correspond in shape and dimension to diaper core 41. It will be understood, however, that the apparatus of FIGS. 1 and 2 can be employed for producing cores of other desired shapes (such as core 51 of FIG. 4) merely by modifying the shape of molds 12 accordingly. Bottom surface 13 of each mold is preferably foraminous, and therefore air will be drawn through bottom surface 13 since the interior of forming drum 11 is maintained under a pressure differential. Forming drum 11 is also mounted for rotation by conventional methods known to those skilled in the art.

Forming Drum 11 further has at least one passageway 14 extending between the endwalls of each pair of adjacent molds. Each passageway 14 extending from one end of a mold 12 is aligned with a similar passageway 14 extending from the opposite end of the mold, such that a plurality of passageways are aligned along a line extending about the entire circumference of drum 11. Multiple passageways 14 may be provided between each pair of adjacent molds, however, each such passageway 14 is aligned with a similar passageway extending from the opposite end of the mold. In this manner, the passageways will be aligned in multiple lines extending about the circumference of drum 11, as shown in FIG. 2 wherein three passageways 14 extend between each pair of adjacent molds. Passageways 14 are preferably open at top surface 15 of forming drum 11, and are no deeper than molds 12. More preferably, passageways 14 are shallower than molds 12, as best shown in FIG. 1.

The apparatus of the present invention further comprises at least one tubular conduit 20, preferably having an arcuate segment 21. Arcuate segment 21 preferably has a curvature corresponding to that of forming drum 11, and is alignably positioned about a portion of the surface of forming drum 11 within one or more molds 12 and the passageways 14 therebetween (as shown in FIG. 2). Since arcuate segment 21 preferably has a curvature corresponding to that of forming drum 11, arcuate segment 21 will preferably be positioned at a predetermined constant depth, and at least partially within molds 12, preferably above bottom surface 13 of the molds. In addition, the alignment of arcuate segment 21 with passageways 14, which are in turn aligned with one another, permits forming drum 11 to freely rotate, with arcuate segment 21 "riding" (preferably in a non-contacting manner) within molds 12 and passageways 14 during rotation. In this manner, arcuate segment 21 will pass from mold to mold through passageways 14 as drum 11 is rotated (arcuate segment 21 preferably remains stationary).

A plurality of tubular conduits 20, each having an arcuate segment 21 and a curvature corresponding to that of the forming drum, are preferably provided, wherein the number of tubular conduits 20 corresponds to the number of passageways 14 extending between adjacent molds, and ultimately the number of strips of second absorbent material desired in the final product. Thus, in the embodiment shown in FIGS. 1 and 2, three such tubular conduits 20 are provided, and each conduit is positioned within one or more molds 12 and a passageway extending between adjacent molds. When only a single conduit is positioned within each passageway, it will be apparent that the spacing between adjacent conduits will correspond approximately to the spacing between adjacent passageways. Alternatively, the passageways between molds may be sized to accommodate more than one conduit.

Figure 6:
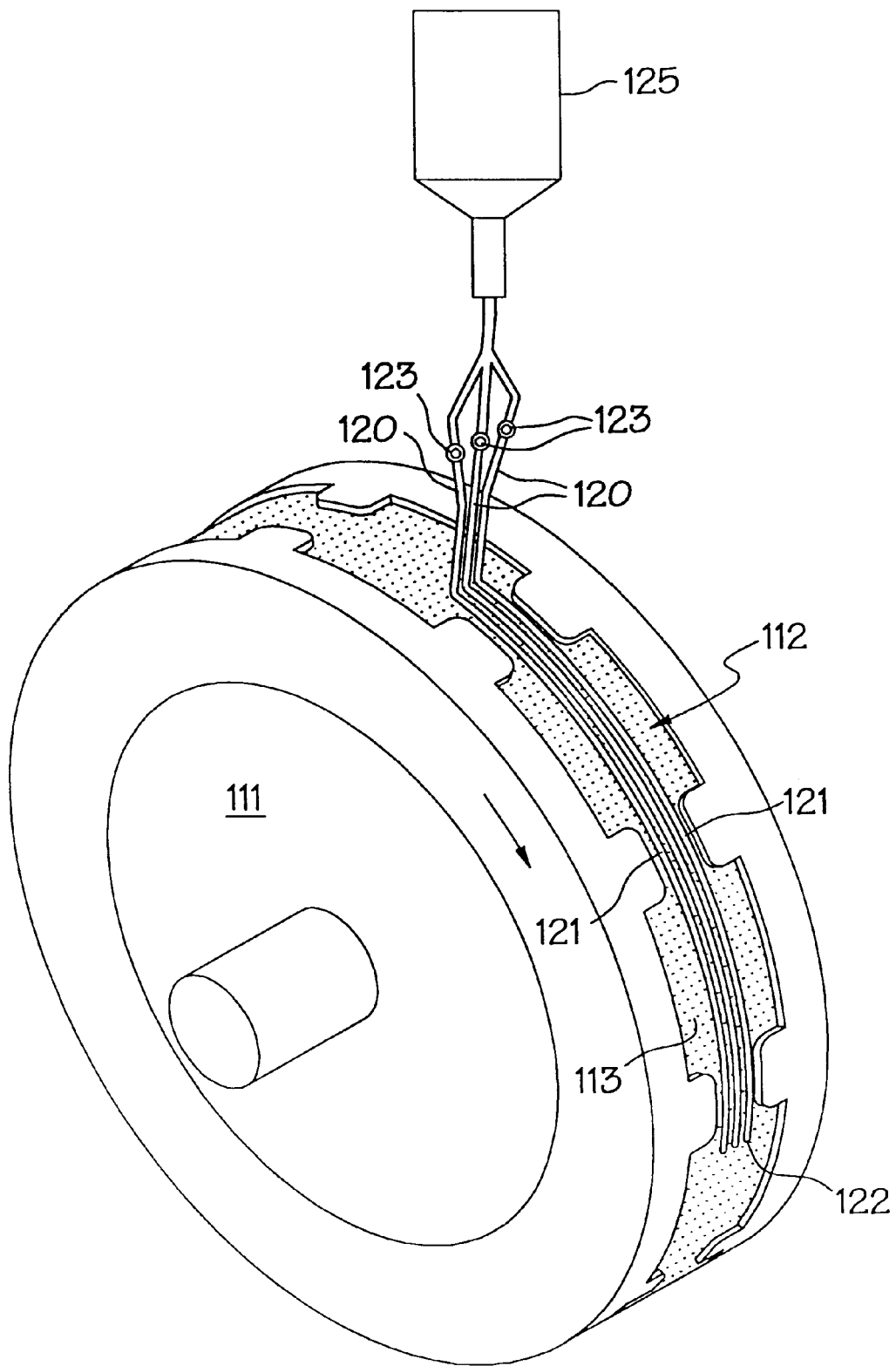
FIG. 6 is a schematic illustration of an alternative embodiment of the forming drum of the present invention.

FIG. 6 depicts an alternative embodiment for the forming drum. In FIG. 6, forming drum 111 has a single mold 112 which extends around at least a portion of the circumference of forming drum 111, preferably around the entire circumference. As will be apparent, this type of forming drum produces a continuous strip of absorbent cores which may later be cut to produce the individual cores of FIG. 3. In essence, therefore, forming drum 111 is similar to forming drum 11 of FIG. 2, wherein the space between the individual molds has been eliminated. Thus, passageways 14 are no longer present. The remaining elements of the embodiment of FIG. 6 are equivalent to those previously described, and thus mold 112 has a foraminous bottom 113, and a plurality of tubular conduits 120 having arcuate segments 121 are also provided.

Each tubular conduit is in fluid communication with a source for the second absorbent material, such as dispenser 25, by conventional means such as piping, tubing, and the like. Dispenser 25 is adapted to store and dispense second absorbent material 43, which can be any material useful for absorption and storage of liquids, and preferably an AGM or a combination of AGM and cellulosic fibers. The second absorbent material is dispensed from dispenser 25 through tubular conduit 20 towards arcuate segment 21, where it subsequently exits conduit 20 at distal end 22. Second absorbent material 43 may be transported from dispenser 25 through tubular conduit 20 by any of a number of conventional means such as air entrainment, particle injectors or spray devices. For example, particularly when the second absorbent material is AGM, the absorbent material may be transported from dispenser 25 through tubular conduit 20 via pulsation or vibration, with or without pressurization of dispenser 25 in order to assist in the transfer of AGM. Transfer of the second absorbent material may also be assisted by gravity. One preferred means for transporting and metering AGM through the tubular conduit is described in International Patent Application WO 96/13335, published on May 9, 1996, which is herein incorporated by reference.

AGM metering may occur prior to the tubular conduits, thereby providing equivalent AGM flow rates through each of the tubular conduits. Alternatively, each of the tubular conduits of the embodiment of FIG. 6 has its own metering device 123. Thus, AGM dispensed from dispenser 125 is separately metered through each of the tubular conduits 120. In this manner, the density of AGM within the strips produced may be varied as desired. In addition, as is more fully described below, AGM may be pulsed through one conduit while continuously urged through another, thereby providing a core having both continuous and discontinuous strips of AGM. It is even possible that different materials may be metered through each of the conduits to provide a core having more than two types of absorbent materials.

The apparatus of the present invention further comprises a deposition chute 30 through which the first absorbent material may be transported for deposition within the molds, such as via fluid-entrainment. Preferably, the first absorbent material is transported via air-entrainment. Deposition chute 30 has a hood 31 which is positioned immediately adjacent forming drum 11 so as to direct the air-entrained fibers or other particles of first absorbent material 42, into molds 12 as forming drum 11 is rotated. Thus, as is well-known in the art, hood 31 is configured to provide a mating relationship with outer surface 15 of forming drum 11. The portion of forming drum 11 which lies directly beneath hood 31 defines an absorbent laydown region 60 having an entrance 58 and an exit 59. First absorbent material 42 is deposited into molds 12 in the absorbent laydown region as the molds 12 move through region 60 from entrance 58 towards exit 59.

When first absorbent material 42 comprises cellulosic fibers such as wood pulp, sheets of cellulosic material may be fed through inlet 34 to a disintegrator 35 (or hammermill), as is known in the art. The sheets of fibrous material are broken down into individual fibers and fiber clumps by disintegrator 35, in order to provide first absorbent material 42 as a "fluff." This fluff then exits disintegrator 35 via duct 36, and is thereafter preferably blown into chute 30 by air entering through air duct 37.

The air-entrained first absorbent material 42, or fluff, is directed by hood 31 into molds 12 of forming drum 11 which are within the absorbent laydown region 60. Since the interior of forming drum 11 is maintained under a pressure differential (i.e., an under pressure or vacuum) and the bottom surface 13 of molds 12 is foraminous, the fluff is deposited into molds 12 of forming drum 11 and held in place by the pressure differential. As forming drum 11 rotates in the manner shown, subsequent molds are similarly filled with fluff in order to form the desired absorbent cores having the shapes of molds 12. After each mold exits from absorbent laydown region 60, one or more scarf rolls 40 and/or one or more calendar rolls remove excess absorbent material from the surface of forming drum 11 and compress the absorbent material within molds 12. Absorbent cores 41 can thereafter be removed from the molds by means of vacuum box 28, with the assistance of gravity, onto transfer conveyor 27. Transfer conveyor 27 thereafter delivers the absorbent cores to further processing apparatus for producing absorbent articles such as diapers, incontinence pads, sanitary napkins, and the like. When the forming drum of FIG. 6 is employed, the cores are produced as a continuous strip which must later be cut into individual cores.

Hood 31 is preferably positioned adjacent to molds 12 in which arcuate segment 21 of tubular conduit 20 is positioned. In this fashion, first absorbent material 42 will be deposited within molds 12 surrounding a significant portion of arcuate segment 21 of tubular conduit 20, thereby effectively providing a cavity within which arcuate segment 21 will be positioned. As mentioned previously, passageways 14 are preferably not as deep as molds 12 (i.e., shallower), and therefore arcuate segments 21 will be positioned at a predetermined distance above bottom surface 13 of the molds. Thus, first absorbent material 42 can even be deposited beneath arcuate segments 21 within molds 12, thereby preferably substantially encompassing the tubular conduit and forming a cavity within the core. This has the added advantage of providing a barrier or filter layer of the fibers of first absorbent material, thereby preventing the second absorbent material from being drawn out of the core and into the interior of the vacuum drum. If desired, the arcuate segments can also be positioned at varying heights above bottom surface 13 of the molds, and the depth of passageways can also be modified accordingly.

After the molds are filled with first absorbent material 42, and after or simultaneous with their exit from beneath hood 31 via the rotation of forming drum 11, second absorbent material 43 can be urged from tubular conduit 20 at distal end 22, and thereafter deposited within the cavity previously formed within first absorbent material 42. In this manner, second absorbent material 43 is deposited in a strip within the absorbent core, wherein the strip has a cross-sectional shape which largely corresponds to that of distal end 22 of tubular conduit 20. The cross-sectional shape of the remainder of the tubular conduit, as well as factors such as fiber collapse may also impact the final cross-sectional shape for the strip of AGM. The apparatus of the present invention may thus be employed to produce absorbent cores having a second absorbent material, such as AGM, present in one or more strips extending substantially lengthwise within and/or through the core.

Arcuate segment 21 of tubular conduit 20 is preferably positioned within the molds and passageways of forming drum 11 within absorbent laydown region 60. Arcuate segment 21 may terminate at distal end 22 either within, or more preferably, immediately beyond the absorbent laydown region. In the embodiment shown in FIG. 1, arcuate segments 21 of tubular conduits 20 terminate just after the absorbent laydown region and prior to scarf roll 40. Arcuate segments 21 should be of sufficient length to insure that first absorbent material 42 will be sufficiently deposited to form the cavity described above, preferably substantially encasing arcuate segment 21 prior to the discharge of the second absorbent material 43. It is also preferable that the arcuate segments extend about the surface of drum 11 from a point just prior to absorbent laydown region 60, as shown, thereby ensuring proper formation of the cavity for the second absorbent material, and minimizing undesired deposition of the first absorbent material.

At times it may be desirable to terminate the arcuate segments within the absorbent laydown region, particularly when the forming drum of FIG. 6 is employed. In this manner, the strips of the second absorbent material may partially collapse and consolidate. Additional first absorbent material may also top off regions formerly occupied by the arcuate segments.

The deposition of the second absorbent material can also be controlled by the intermittent urging from the distal end of the tubular conduit, particularly by means of the apparatus and methods disclosed in WO 96/13335. For example, the movement of second absorbent material 43 through tubular conduit 20 can be timed such that the second absorbent material is deposited in one or more discontinuous strips comprising a plurality of co-linear segments along the path of the cavity formed by tubular conduit 20 resulting in a core of the type depicted in FIG. 5. In this instance, arcuate segments 21 may terminate at distal end 22 within the absorbent laydown region such that the region between the colinear segments of each strip may be filled-in with the first absorbent material. Pads having discontinuous, co-linear segments or strips of AGM may be desired for maximizing pad performance or efficiency (i.e., reducing the amount of AGM needed).

Tubular conduit 20 may be constructed of a variety of rigid materials such as metals, plastic, or composites, and is preferably constructed from stainless steel. A variety of cross-sectional shapes may also be employed for tubular conduit 20 and/or distal end 22, including round, circular, rectangular, concave or convex crescent-shaped, ovate, obround or flattened oval, depending on the desired shape of the strips of second absorbent material 43, and to facilitate transport of the absorbent material through the conduit.

In order to avoid inadvertent adhesion or buildup of absorbent material on either the inside or outside of tubular conduit 20, both the inside and outside surfaces of tubular conduit 20 are preferably smooth and/or polished. Various types of non-slip coatings such as Teflon or silicon also may be applied to the surfaces of conduit 20, as desired. Additionally, the pulsation or vibration of tubular conduit 20 previously mentioned can be employed to continuously "shake" absorbent material from both the inside and outside of tubular conduit 20. Ultrasonic pulsations or vibrations may even be employed for this purpose, and these vibrations may even be tuned to avoid contact between the conduit and the passageways 14. Alternatively, electrostatic repulsion may also be implemented to assist in preventing adhesion or buildup, wherein the absorbent materials and tubular conduit 20 are charged in order to repulse each other.

One particular advantage of the apparatus and method of the present invention is that second absorbent material 43 may be provided in the absorbent cores at any desired location. For example, the depth of the strips of second absorbent material 43 may be modified merely by adjusting the depth of passageways 14. In addition, any of a number of tubular conduits 20 may be provided, and each may be positioned in any desired location of the absorbent core. The method and apparatus of the present invention is particularly advantageous when AGM is employed as the second absorbent material, either alone or in combination with other absorbent materials, since the AGM can be applied to precise locations within the core thereby resulting in a lower cost and improved core performance. Additionally, the apparatus of the present invention will minimize costly AGM dust-handling equipment, as the loss of AGM will be minimized. This contrasts to conventional AGM distribution systems, wherein AGM particles are homogeneously mixed with air-entrained fiber streams resulting in a highly random distribution of AGM in the core. Such AGM distributions have proven inefficient. With the apparatus and method of the present invention, the AGM is placed only in the most desirable locations of the absorbent core, thereby resulting in an absorbent article of improved performance.

Figure 7:
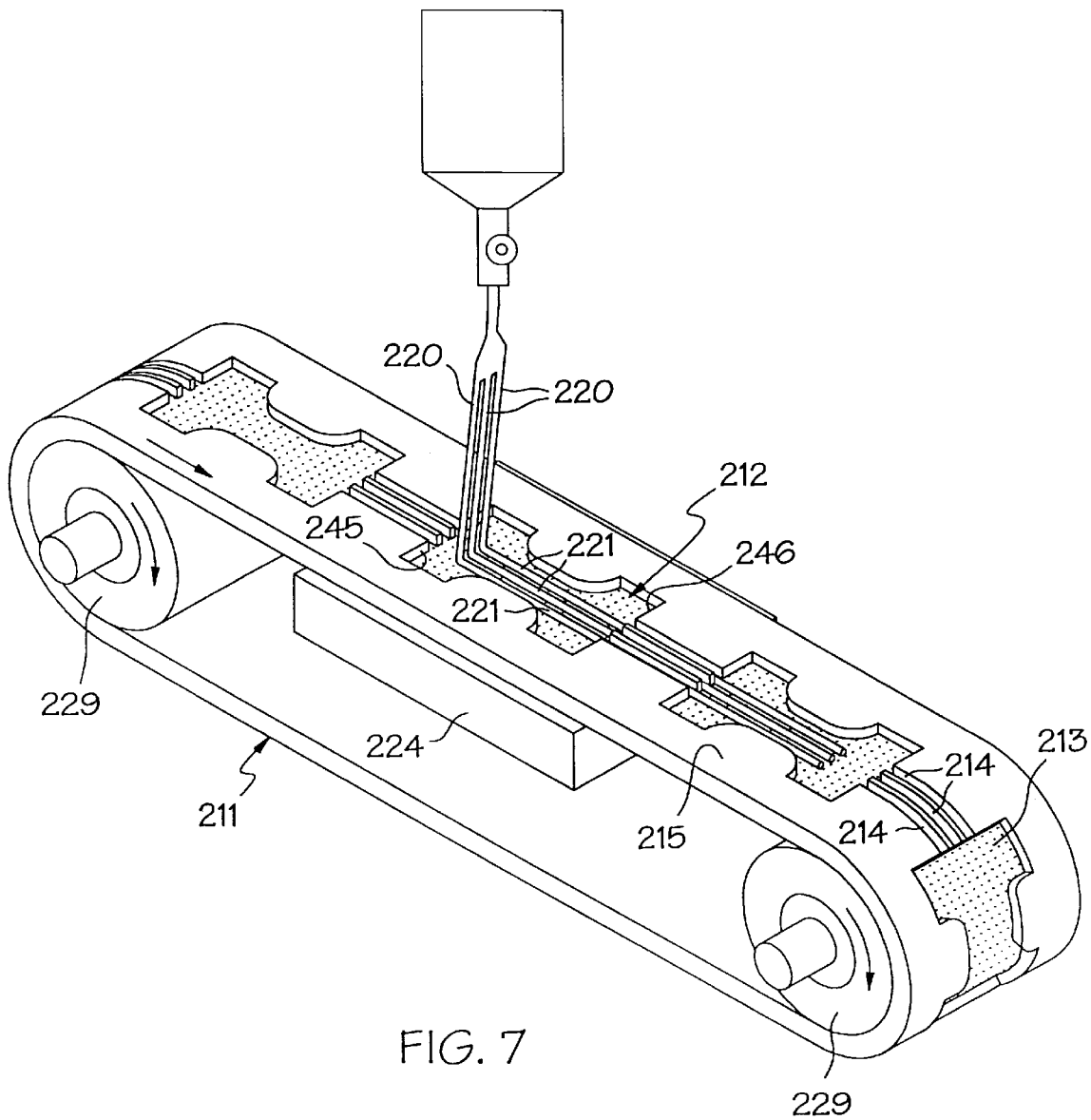
FIG. 7 is a schematic illustration of a forming belt which may be employed in the apparatus and method of the present invention instead of a forming drum.

FIG. 7 depicts yet another embodiment for the mold support of the present invention. In FIG. 7, the mold support comprises a forming belt 211, which is preferably advanceable in a closed loop fashion. Forming belt 211 is tensioned between two or more rotatable drums in the manner known to those skilled in the art, and can be driven by conventional means. While forming belt 211 is shown as being positioned horizontally, various other configurations can be employed. Thus, forming belt 211 can even be positioned vertically or diagonally. Forming belt 211 has a plurality of molds 212 in its top surface 215, each of these molds having a foraminous bottom 213, and first and second endwalls 245 and 246, respectively. In a manner similar to that in the forming drum of FIGS. 1–2, at least one passageway 214 extends between the endwalls of each pair of adjacent molds. Preferably, a plurality of passageways 214 extend between adjacent endwalls, and each such passageway is aligned with a similar passageway extending from the opposite end of the mold. A vacuum box 224 or other equivalent device is positioned beneath one or more of the molds in order to provide the necessary pressure differential.

As will be apparent, the apparatus of FIG. 7 may be employed in a manner nearly identical to the forming drums previously described. In this case, however, the tubular conduits need not have an arcuate segment, since the tubular conduits may be positioned within one or more of the molds 212 on the flat portion of forming belt 211 positioned directly above vacuum box 224. Thus, tubular conduits 220 each have a linear segment 221 alignably positioned within one or more of molds 212 and/or passageways 214 above vacuum box 224. As forming belt 211 is advanced in the direction shown, linear segments 221 will "ride" within molds 212 and passageways 214 in a manner similar to that described for the forming drum of FIG. 2. Since forming belt 211 also curves about drums 229, however, tubular conduits 220 can be provided with arcuate segments which are positioned adjacent forming belt 211 at the curved region of the belt (such as above drum 229). In this embodiment, forming belt 211 will essentially be equivalent to the forming drums previously described. Thus, tubular conduits 220 should each have a segment which corresponds in curvature to that of the forming belt in the region wherein the second absorbent material is to be deposited. In the specific embodiment of FIG. 7, this curvature is zero (i.e., linear). A hood for directing the first absorbent material into molds 212 may also be positioned above vacuum box 224. As will be apparent, forming belt 211 may also be provided with a single mold, similar to FIG. 6.

The foregoing description of preferred embodiments is by no means exhaustive of the variations in the present invention that are possible, and has been presented only for purposes of illustration and description. Obvious modifications and variations will be apparent to those skilled in the art in light of the teachings of the foregoing description. For example, the location of arcuate segments 21 of tubular conduits 20 may be varied in order to achieve optimal performance. Arcuate segments 21 may even be placed at several different depths within mold 12, thereby producing an absorbent core having the second absorbent material positioned at varying depths. Thus, it is intended that the scope of the present invention be defined by the claims appended hereto.

What is claimed is:

1. A method of producing absorbent cores containing a dispersed first absorbent material and a second absorbent material present in at least one strip within said first material, said method comprising:

(a) providing a mold support having at least one mold therein;

(b) providing a tubular conduit for said second material, said conduit alignably positioned such that a portion of said conduit will pass through at least a portion of said mold as said mold support is advanced in a predetermined direction, said tubular conduit further having a distal end through which said second absorbent material may be expelled;

(c) providing a deposition chute adjacent said mold support for presenting said first absorbent material to said mold;

(d) conducting a stream of fluid-entrained particles of said first absorbent material through said chute into said mold as said mold support is advanced, such that said first absorbent material is deposited at least partially about the circumference of a portion of said tubular conduit; and (e) urging said second absorbent material through said tubular conduit and out said distal end for deposition within said mold.

2. The method of claim 1, wherein said mold support comprises a forming belt.

3. The method of claim 1, wherein said mold support comprises a rotatable forming drum, wherein said mold extends about at least a portion of the circumference of said forming drum, and wherein said tubular conduit has an arcuate segment which extends about a portion of said drum and is alignably positioned such that said arcuate segment will pass through said mold as said drum is rotated.

4. The method of claim 3, wherein said forming drum has a plurality of molds about its circumference, each of said molds having endwalls and a bottom surface, said drum further having a passageway extending between the endwalls of each pair of adjacent molds, wherein said passageways are circumferentially aligned with one another, and wherein said arcuate segment passes from mold to mold through said passageways as said drum is rotated.

5. The method of claim 4, wherein said first absorbent material is deposited around at least a substantial portion of the circumference of said arcuate segment, thereby forming a cavity into which said second absorbent material is deposited.

6. The method of claim 4, wherein said second absorbent material is intermittently urged out said distal end of said conduit such that said second absorbent material is deposited within said molds as a discontinuous strip comprising a plurality of co-linear segments.

7. The method of claim 4, wherein said second absorbent material comprises an absorbent gelling material.

8. The method of claim 7, wherein said first absorbent material comprises cellulosic fibers.

9. The method of claim 4, wherein said deposition chute has a hood positioned adjacent said forming drum and configured so as to direct air-entrained particles of said first absorbent material into said molds as said forming drum is rotated, wherein the portion of said forming drum beneath said hood defines an absorbent laydown region having an entrance and an exit, wherein normal rotation of said drum causes said molds to move through said absorbent laydown region from said entrance towards said exit, and wherein said tubular conduit are is configured such that the arcuate segment extends about said drum from a point prior to the entrance of said absorbent laydown region.

10. The method of claim 9, wherein said second absorbent material is urged out of said tubular conduit into said cavity at a point beyond said absorbent laydown region.

11. The method of claim 2, wherein said mold support comprises a continuous and advanceable forming belt.

12. The method of claim 4, wherein a plurality of tubular conduits and a plurality of passageways between the endwalls of adjacent molds are provided, said conduits alignably positioned such that a portion of said conduits will pass through at least a portion of said molds and passageways as said drum is rotated.

13. The method of claim 1, further comprising providing a dispenser in fluid communication with the conduit.

14. The method of claim 9, wherein said arcuate segment terminates within the absorbent laydown region.

15. A method of producing absorbent cores containing a dispersed first material and a second material present in at least one strip, said method comprising:

(a) providing a mold support having at least one mold;

(b) providing at least one tubular conduit positioned such that a portion of the tubular conduit will pass through at least a portion of said mold as the mold support is advanced in a predetermined direction, said tubular conduit further having a distal end;

(c) depositing said first material into said mold; and (d) urging said second material through said tubular conduit and out said distal end as said mold support is advanced such that a strip of said second material is deposited in said mold.

16. The method of claim 15, wherein the mold support comprises a rotatable drum which is advanceable by rotation of said drum, and wherein the tubular conduit comprises an arcuate segment which extends about a portion of said drum and is alignably positioned such that said arcuate segment will pass through said mold as said drum is rotated.

17. The method of claim 16, wherein the arcuate segment has a length equal to or greater than said mold.

18. The method of claim 15, wherein the mold extends the circumference of said forming drum.

19. The method of claim 17, comprising a plurality of tubular conduits further comprising arcuate segments wherein the arcuate segments are positioned at different heights above the molds.

* * * * *